US012685770B2

(12) United States Patent
Rhee et al.

(10) Patent No.: US 12,685,770 B2
(45) Date of Patent: Jul. 21, 2026

(54) DEIMMUNIZED FLAGELLIN AND VACCINE COMPOSITION COMPRISING SAME

(71) Applicant: FlagImmune, Jeollanam-do (KR)

(72) Inventors: Joon Haeng Rhee, Gwangju (KR);
Shee Eun Lee, Gwangju (KR);
Koemchhoy Khim, Jeollanam-do (KR);
Sao Puth, Jeollanam-do (KR)

(73) Assignee: FlagImmune, Jeollanam-do (KR)

( * ) Notice: Subject to any disclaimer, the term of this patent is extended or adjusted under 35 U.S.C. 154(b) by 355 days.

(21) Appl. No.: 18/568,069

(22) PCT Filed: Jun. 29, 2022

(86) PCT No.: PCT/KR2022/009321
§ 371 (c)(1),
(2) Date: Dec. 7, 2023

(87) PCT Pub. No.: WO2023/282530
PCT Pub. Date: Jan. 12, 2023

(65) Prior Publication Data
US 2024/0277837 A1     Aug. 22, 2024

(30) Foreign Application Priority Data

Jul. 9, 2021     (KR) ........................ 10-2021-0090501

(51) Int. Cl.
| | |
|---|---|
| *A61K 39/39* | (2006.01) |
| *A61K 39/00* | (2006.01) |
| *A61K 39/145* | (2006.01) |
| *A61P 31/16* | (2006.01) |
| *C07K 14/28* | (2006.01) |

(52) U.S. Cl.
CPC .............. *A61K 39/39* (2013.01); *A61K 39/00* (2013.01); *A61K 39/145* (2013.01); *A61P 31/16* (2018.01); *C07K 14/28* (2013.01); *A61K 2039/55516* (2013.01)

(58) Field of Classification Search
None
See application file for complete search history.

(56) References Cited

U.S. PATENT DOCUMENTS

2025/0263450 A1*  8/2025  Cho ........................ A61K 39/00

FOREIGN PATENT DOCUMENTS

| KR | 10-2007-0017300 A | 2/2007 |
|---|---|---|
| KR | 10-2017-0031251 A | 3/2017 |
| KR | 10-2020-0123751 A | 10/2020 |

OTHER PUBLICATIONS

Biedma M., et al. Recombinant flagellins with deletions in domains D1, D2, and D3: Characterization as novel immunoadjuvants, Vaccine 37 (2019) 652-663, published Dec. 21, 2018 (Year: 2018).*
Holbrook, B., et al. Adjuvating an inactivated influenza vaccine with flagellin improves the function and quantity of the long-term antibody response in a nonhuman primate neonate model, Vaccine, vol. 34, Iss 39, published Sep. 7, 2016 (Year: 2016).*
Jia, P., et al, Comparative study of four flagellins of Vibrio anguillarum: Vaccine potential and adjuvanticity, Fish & Shellfish Immunology 34 (2013) 514-520, published Dec. 16, 2012 (Year: 2012).*
Lee, S., et al, A Bacterial Flagellin, Vibrio vulnificus FlaB, Has a Strong Mucosal Adjuvant Activity to Induce Protective Immunity, Infection and Immunity, vol. 74, No. 1, published Jan. 2006 (Year: 2006).*
Cote-Cyr, M. et al. Recombinant Bacillus subtilis flagellin Hag is a potent immunostimulant with reduced proinflammatory properties compared to *Salmonella enterica* serovar Typhimurium FljB, Vaccine 40 (2022) 11-17, published Nov. 26, 2021 (Year: 2022).*
Faber, E., et al, Novel Immunomodulatory Flagellin-Like Protein FlaC in Campylobacter jejuni and Other Campylobacterales, mSphere 1(1):00028-15, published Dec. 2, 2015 (Year: 2015).*
Mukherjee, S. et al, The structure and regulation of flagella in Bacillus subtilis, Annual Review Genetics. 48:319-340, published Nov. 2014 (Year: 2014).*
Biedma, M.,E., et al.; "Recombinant flagellins with deletions in domains D1, D2, and D3Characterization as novel immunoadjuvants", Vaccine, 2019, vol. 37, pp. 652-663.
International Search Report from corresponding PCT Application No. PCT/KR2022/009321 dated Oct. 12, 2022.

* cited by examiner

*Primary Examiner* — Bao-Thuy L Nguyen
*Assistant Examiner* — Bonirath Chhay
(74) *Attorney, Agent, or Firm* — Harness, Dickey & Pierce, P.L.C.

(57)     ABSTRACT

The present invention relates to: deimmunized flagellin that does not induce the production of flagellin-specific antibodies; and use thereof. In particular, the present invention relates to a flagellin variant in which a major epitope that forms an antibody against flagellin is deleted, the flagellin variant being characterized by, when used as a vaccine adjuvant, not producing antibodies against flagellin while maintaining an excellent immune enhancer effect.

7 Claims, 11 Drawing Sheets

Specification includes a Sequence Listing.

DEIMMUNIZED FLAGELLIN AND VACCINE COMPOSITION COMPRISING SAME

CROSS-REFERENCE TO RELATED APPLICATIONS

This application is a national phase application of PCT Application No. PCT/KR2022/009321, filed on Jun. 29, 2022, which claims priority to Korean Patent Application No. 10-2021-0090501, filed on Jul. 9, 2021. The entire disclosures of the applications identified in this paragraph are incorporated herein by references.

This application contains references to amino acid sequences and/or nucleic acid sequences which have been submitted concurrently herewith as the sequence listing TXT file entitled "000354usnp_SequenceListing.txt", file size 617 bytes, created on 7 Dec. 2023. The aforementioned sequence listing is hereby incorporated by reference in its entirety pursuant to 37 C.F.R. § 1.52(e)(5).

TECHNICAL FIELD

The present invention relates to a deimmunized flagellin and a vaccine composition containing the same. Specifically, the present invention relates to a flagellin variant in which a major epitope for an antibody against flagellin is deleted and a vaccine composition containing the same, wherein the use of the flagellin variant as a vaccine adjuvant does not produce an antibody against flagellin while maintaining an excellent immune booster effect.

BACKGROUND ART

Vaccines activate the body's immune system by the injection of artificially inactivated (pathogenicity-eliminated) or attenuated (pathogenicity-weakened) pathogens into the human body before infection with pathogens, thus preventing or minimizing the damage caused by the pathogens even if the human body is later infected with the pathogens. In other words, the weakening and injecting of viruses causing diseases allows the immune cells of our bodies to form antibodies to develop immunity to the viruses, leading to the prevention of diseases.

Vaccines are mainly administered intramuscularly or subcutaneously but, in some cases like in flu vaccines, administered to the nasal mucosa. Such vaccines allowing for mucosal administration are called mucosal vaccines. The administration of vaccines through mucosal routes has the advantage of simultaneously promoting not only systemic immune response but also "mucosal immune response". This is amplifying the interest on research about the development of preventive vaccines capable of inducing effective immune responses in mucosal tissues. However, the administration of most protein antigens by mucosal routes has the disadvantage of reducing immunogenicity compared with systemic administration routes. Therefore, the development of effective mucosal immune adjuvants that can be safely administered together with vaccine antigens is most important to develop mucosal vaccines.

Immune adjuvants are components that serve to produce antibodies and enhance immune responses by the immune system and are also called as immune boosters or antigen enhancers. That is, the immune adjuvants are known to serve to increase immunogenicity against antigens used in vaccines and regulate characteristics of the immune responses. Currently clinically used immune boosters are alum, MF59 as an oil-water emulsion containing squalene, ASO3 as another emulsion, ASO4 as a composite immune booster in which monophosphoryl lipid A (MPL) as a TLR4 agonist is added to alum, and the like. Various immune boosters including glucopyranosyl lipid adjuvant-stable emulsion (GLA-SE) are also in clinical trials. Although many immune boosters have been developed as such, there is a continuous need for the development of new immune adjuvants that can provide more satisfactory performance.

Meanwhile, a structural unit protein constituting filaments of flagella is called flagellin, and filaments are formed by regular assembly of flagellin and enable bacteria to move. This flagellin has been studied as a target for the development of vaccine carrier proteins or vaccine adjuvants since it serves as the first line of defense against flagellate-pathogenic bacteria. A fusion protein of an antigen and flagellin has been demonstrated to be effective as an experimental vaccine against a variety of contagious diseases including West Nile fever, malaria, infectious diseases, and tuberculosis, and it has been reported that flagellin-induced TLR5 activation also protects hematopoietic cells and radiation-induced gastrointestinal tissue and affects the survival and growth of cancer cells. The present inventors verified in Korean Patent No. 10-0795839 that flagellin (FlaB) as a constituent component of *Vibrio vulnificus* had excellent mucosal vaccine adjuvant efficacy by acting on toll-like receptor 5 of host cells to induce a potent immunoregulatory effect.

However, flagellin is a protein and thus can exhibit efficacy as a vaccine adjuvant or immune booster as well as may induce the immune response to flagellin itself. That is, the administration of flagellin in combination with another antigen for the purpose as an immune booster may produce antibodies against to flagellin itself. Therefore, the repeated administration of a vaccine formulation containing a flagellin immune adjuvant has the problem that already formed antibodies against flagellin may reduce the effect of additionally administered flagellin immune adjuvants.

Accordingly, in order to develop flagellin not producing an antibody against flagellin while maintaining an immune booster effect, the present inventors developed deimmunized flagellin in which a major epitope for an antibody against flagellin is deleted, and completed the present invention.

PRIOR ART DOCUMENT

Patent Document (Patent Document 1) Korean Patent No. 10-0795839

DETAILED DESCRIPTION OF THE INVENTION

Technical Problem

An aspect of the present invention is to provide a flagellin variant in which a major epitope for an antibody against flagellin is deleted.

Another aspect of the present invention is to provide a deimmunized flagellin not producing an antibody against flagellin while maintaining an excellent immune booster effect when used as a vaccine adjuvant, and a vaccine composition containing the same.

Technical Solution

In accordance with an aspect of the present invention, there is provided a flagellin variant in which a major epitope for an antibody against flagellin is deleted.

In accordance with another aspect of the present invention, there is provided a flagellin variant in which N-terminal domain 2, domain 3, and C-terminal domain 2; or the amino acid sequence of SEQ ID NO: 1 is deleted in flagellin or a fragment thereof.

In the present invention, the fragment may include at least one selected from the group consisting of: N-terminal domain 0, N-terminal domain 1, N-terminal domain 2, domain 3, C-terminal domain 2, C-terminal domain 1, and C-terminal domain 0 of wild-type flagellin; and a domain showing at least 80% amino acid sequence homology to each of the domains of wild-type flagellin.

The flagellin of the present invention may be derived from a microorganism selected from the group consisting of the genera *Bacillus, Salmonella, Helicobacter, Vibrio, Serratia, Shigella, Treponema, Legionella, Borrelia, Clostridium, Agrobacterium, Bartonella, Proteus, Pseudomonas, Escherichia, Listeria, Yersinia, Campylobacter, Roseburia,* and *Marinobacter.*

The flagellin of the present invention may be derived from a microorganism selected from the group consisting of *Salmonella enteritidis, Salmonella typhimurium, Salmonella dublin, Salmonella enterica, Helicobacter pylor, Vibrio cholera, Vibrio vulnificus, Vibrio fibrisolvens, Serratia marcesens, Shigella flexneri, Treponema pallidum, Borrelia burgdorferei, Clostridium difficile, Agrobacterium tumefaciens, Bartonella clarridgeiae, Proteus mirabilis, Bacillus subtilis, Bacillus cereus, Bacillus halodurans, Pseudomonas aeruginosa, Escherichia coli, Listeria monocytogenes, Yersinia pestis, Campylobacter* spp., *Roseburia* spp., and *Marinobacter* spp.

Preferably, the flagellin may be derived from *Vibrio vulnificus.*

The flagellin of the present invention may be flagellin B (FlaB).

The flagellin variant of the present invention has an immune boosting effect by retaining toll-like receptor 5 (TLR5) stimulatory activity and inducing no flagellin-specific immune response.

In accordance with still another aspect of the present invention, there is provided a nucleic acid encoding the flagellin variant.

In accordance with still another aspect of the present invention, there is provided a recombinant vector including the nucleic acid or having the nucleic acid inserted therein.

In accordance with still another aspect of the present invention, there is provided a host cell transformed with the nucleic acid.

In accordance with still another aspect of the present invention, there is provided a vaccine composition containing the flagellin variant and at least one antigen.

In accordance with still another aspect of the present invention, there is provided a flu vaccine composition containing the flagellin variant as an adjuvant.

Advantageous Effects

The administration of the deimmunized flagellin according to the present invention in combination with another antigen for the purpose as an immune booster does not produce an antibody against flagellin while maintaining an excellent immune booster effect of flagellin, so that the deimmunized flagellin can be very advantageously used as a vaccine adjuvant.

Furthermore, the administration of the deimmunized flagellin according to the present invention in combination with a flu vaccine can induce better protective immunity compared with the flu vaccine containing wild-type flagellin.

BRIEF DESCRIPTION OF THE DRAWINGS

FIG. 1 schematically shows deimmunized flagellin variants of the present invention.

FIG. 2 shows the results of BepiPred 2.0, Parker hydrophilicity, and alanine scanning for identifying the B-cell epitope of FlaB.

FIG. 4 shows NF-ζB activity levels indicating TLR5 signaling degrees of FlaB, dFlaB, and FlaBΔD2D3.

MODE FOR CARRYING OUT THE INVENTION

Figure 3:
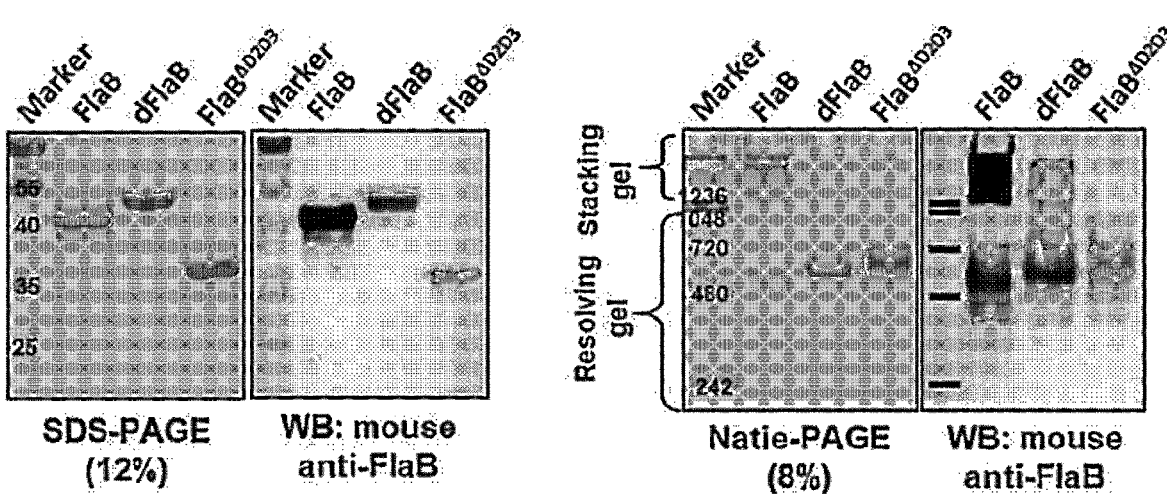
FIG. 3 shows SDS-PAGE, native-PAGE, and Western blotting results of FlaB, dFlaB, and FlaBΔD2D3.

Hereinafter, embodiments and examples of the present application will be described in detail with reference to the accompanying drawings so that a person skilled in the art to which the present invention pertains can easily implement the present application. However, the present application can be implemented in various forms and is not limited to the embodiments and examples described herein.

Throughout the specification of the present application, unless otherwise stated, when a certain part "includes", "contains", or "comprises" a certain element, it means that the certain part may further include or comprise other elements rather than exclude other elements.

The present invention is directed to a deimmunized flagellin and a vaccine composition containing the same.

The present invention provides a deimmunized flagellin characterized in that the use of a vaccine adjuvant, in which a major epitope for an antibody against flagellin is deleted, as a vaccine adjuvant does not produce an antibody against flagellin while maintaining an excellent immune booster effect.

The deimmunized flagellin of the present invention is a flagellin variant in which N-terminal domain 2, domain 3, and C-terminal domain 2; or the amino acid sequence of SEQ ID NO: 1 is deleted in flagellin or a fragment thereof.

The deimmunized flagellin of the present invention retains toll-like receptor 5 (TLR5) stimulatory activity and does not induce a flagellin-specific immune response, and thus has an immune boosting effect.

As used herein, the term "flagellin" refers to a main protein constituting bacterial flagellar filaments, and when a flagellated bacterium is infected, the flagellin may induce an immune response within the infected host. Specifically, toll-like receptor 5 (TLR5) present on the cell membrane surface of the human body can induce intracellular signaling through the interaction with the flagellin, and through this, the expression of NF-ζB, a transcription factor, is increased to induce the activation of innate immune signals, as well as regulate acquired immune responses.

The flagellin includes two to four domains. For example, *Bacillus subtilis* Hag flagella, *Pseudomonas aeruginosa* type-A FliC flagella, and *Salmonella enterica* subspecies *enterica* serovar Typhimurium FliC flagellin contain two (D0 and D1), three (D0, D1, and D2), and four (D0, D1, D2, and D3) domains, respectively. The D0 and D1 domains common in these are located at the center of flagellar filaments by mediating inter-flagella interactions and are highly conserved among bacterial species due to the functional importance of filament formation. Since the flagellin monomer, not a polymerized filament of flagellin, activates TLR5, it is considered that D0 and D1 domains may be major stimulators of TLR5. However, D2 and D3 domains show substantial changes in the sequences and structures and are considered to activate adaptive immunity and induce undesirable toxicity in flagellin-based therapies.

As used herein, the "flagellin" or "wild-type flagellin" may include N-terminal domain 0 (ND0), N-terminal domain 1 (ND1), N-terminal domain 2 (ND2), domain 3 (D3), C-terminal domain 2 (CD2), C-terminal domain 1 (CD1), and C-terminal domain 0 (CD0).

In an embodiment, the flagellin of the present invention may be flagellin B (FlaB), and the flagellin B (FlaB) includes four domains: D0, D1, D2, and D3.

The flagellin may include full-length flagellin or a fragment thereof. In addition, the terms "flagellin", "flagellin N-terminal region", and "flagellin C-terminal region" include a naturally occurring amino acid sequence, or may also include an amino acid sequence substantially identical or similar to an amino acid sequence of a naturally occurring flagellin, flagellin N-terminal region, or flagellin C-terminal region, respectively.

The fragment may be a fragment including at least one selected from the group consisting of: N-terminal domain 0, N-terminal domain 1, N-terminal domain 2, domain 3, C-terminal domain 2, C-terminal domain 1, and C-terminal domain 0 of wild-type flagellin; and a domain showing at least 80% amino acid sequence homology to each of the domains of wild-type flagellin.

In an embodiment, the flagellin may be derived from a microorganism selected from the group consisting of *Bacillus, Salmonella, Helicobacter, Vibrio, Serratia, Shigella, Treponema, Legionella, Borrelia, Clostridium, Agrobacterium, Bartonella, Proteus, Pseudomonas, Escherichia, Listeria, Yersinia, Campylobacter, Roseburia*, and *Marinobacter*.

In an embodiment, the flagellin may be derived from a microorganism selected from the group consisting of *Salmonella enteritidis, Salmonella typhimurium, Salmonella dublin, Salmonella enterica, Helicobacter pylor, Vibrio cholera, Vibrio vulnificus, Vibrio fibrisolvens, Serratia marcesens, Shigella flexneri, Treponema pallidum, Borrelia burgdorferei, Clostrdium difficile, Agrobacterium tumefaciens, Bartonella clarridgeiae, Proteus mirabilis, Bacillus subtilis, Bacillus cereus, Bacillus halodurans, Pseudomonas aeruginosa, Escherichia coli, Listeria monocytogenes, Yersinia pestis, Campylobacter* spp., *Roseburia* spp., and *Marinobacter* spp., and may be preferably derived from *Vibrio vulnificus*.

As used herein, the term "deimmunization" or "deimmunized" refers to the reduction of immunogenicity of antibodies, and may be caused by modifying a wild-type structure to be non-immunogenic or less immunogenic compared with the original wild-type structure.

Furthermore, the present invention provides: a nucleic acid encoding the flagellin variant; and a recombinant vector including the nucleic acid or having the nucleic acid inserted therein.

Examples of the vector include a plasmid vector, a cosmid vector, a bacteriophage vector, and a viral vector, but are not limited thereto. The vector of the present invention may be a conventional cloning vector or expression vector. The expression vector may include a signal sequence or leader sequence for membrane targeting or secretion, in addition to expression control sequences, such as a promoter, an operator, an initiation codon, a termination codon, a polyadenylation signal, and an enhancer (promoter gene), and may be variously prepared according to the purpose.

Furthermore, the present invention provides a host cell transformed with the nucleic acid.

The transformed host cell may mean a prokaryotic or eukaryotic cell including heterogeneous DNA introduced into the cell by any means (e.g., an electric shock method, a calcium phosphatase precipitation method, a micro-injection method, a transformation method, viral infection, etc.).

Furthermore, the present invention provides a vaccine composition including the flagellin variant and at least one antigen.

As used herein, the term "vaccine" refers to the meaning encompassing preventing the infection or re-infection with a corresponding pathogen, reducing the severity of symptoms or eliminating symptoms by a corresponding pathogen, or substantially or completely removing a corresponding pathogen or a disease by the pathogen, by inducing an immune response to the corresponding pathogen in an animal including a human host. Thus, the "vaccine composition" of the present invention may be administered, to an animal including a human, prophylactically before infection with the corresponding pathogen, or therapeutically after infection with the corresponding pathogen.

The vaccine composition of the present invention may be prepared in any appropriate, pharmaceutically acceptable formulation. For example, the vaccine composition may be prepared in the form of an immediately administrable solution or suspension, or a concentrated crude solution suitable for dilution before administration, or in a form capable of being reconstituted, such as a lyophilized, freeze-dried, or frozen formulation.

The vaccine composition of the present invention may be formulated while containing a pharmaceutically acceptable carrier. The pharmaceutically acceptable carrier may typically include a diluent, an excipient, a stabilizer, a preservative, and the like. Examples of the diluent that may be included in the vaccine composition of the present invention may include non-aqueous solvents, such as propylene glycol, polyethylene glycol, and vegetable oil including olive oil and peanut oil, or aqueous solvents, such as saline and water containing a buffer medium. Examples of the excipient may include starch, glucose, lactose, sucrose, gelatin, malt, rice, flour, chalk, silica gel, sodium stearate, glycerol monostearate, talc, sodium chloride, anhydrous skim milk, glycerol, propylene, glycol, water, ethanol, and the like. Examples of the stabilizer may include carbohydrates, such as sorbitol, mannitol, starch, sucrose, dextran, glutamate, and glucose, or proteins, including animal, vegetable or microbial proteins, such as milk powder, serum albumin, and casein. Examples of the preservative may include thimerosal, merthiolate, gentamicin, neomycin, nystatin, amphotericin B, tetracycline, penicillin, streptomycin, polymyxin B, and the like.

The vaccine composition of the present invention may be parenterally or orally administered according to a desired method, and the dose thereof may be varied according to the weight, age, sex, and health condition of a patient, a diet, the time of administration, method of administration, rate of excretion, severity of disease, and the like. The prophylactically or therapeutically effective amount of the composition may vary depending on the method of administration, target site, and patient's condition, and when used in the human body, the dose thereof should be determined at an appropriate amount in consideration of both safety and efficiency.

Furthermore, the present invention provides a flu composition containing the flagellin variant as an adjuvant.

As used herein, the term "adjuvant" refers to a substance or composition, which may be added to vaccines or pharmaceutically active components to increase or affect the immune response. The adjuvant typically means a carrier or auxiliary substance for an immunogen and/or another pharmaceutically active material or composition. In general, the term "adjuvant" should be interpreted in a broad sense, and refers to a wide range of substance or stratagem that can enhance the immunogenicity of an antigen incorporated into the adjuvant or administered together with the adjuvant. In addition, adjuvants may be divided into an immune potentiator, an antigen delivery system, or a combination thereof, but are not limited thereto.

The vaccine adjuvant in the present invention may be in the form of a solution, suspension, or emulsion in an oil or aqueous medium, may be prepared as an oral formulation in a sterile state before use or a dried powder type that is dissolved in pyrogen-free water at use, and may be formulated as a non-oral formulation, such as subcutaneous injection, intravenous injection, or intramuscular injection.

Specific examples of the "vaccine adjuvant" in the present invention may be adjuvants for: anti-toxin vaccines against tetanus and the like; live and killed vaccines against cholera, typhoid fever, and the like; anti-viral vaccines against influenza, SARS, and the like; anti-cancer vaccines against uterine cervix cancer and the like; anti-sperm contraceptive vaccines; and recombinant vaccines of proteins or peptides, but are not limited thereto.

The vaccine adjuvant of the present invention may be prepared by a conventional method well known in the art, and may optionally further contain several additives that can be used in the production of vaccines in the art.

As used herein, the term "immune response" refers to a humoral immune response, a cellular immune response, or both of these.

As used herein, the term "antibody" refers to an immunoglobulin which is natural or partly or wholly synthetically produced. The term also covers any polypeptide or protein including an antigen-binding domain of an antibody. Antibody fragments including an antigen-binding domain are molecules, such as Fab, scFv, Fv, dAb, Fd, and diabodies. The term "antibody" is used in a broad sense, and specifically covers intact monoclonal antibodies, polyclonal antibodies, multispecific antibodies (e.g., bispecific antibodies) formed from at least two intact antibodies, and the term covers antibody fragments so long as they exhibit the desired biological activity.

As used herein, the term "B cell" refers to an immune cell that protects the human body from pathogenic microorganisms, cancer cells, and the like by recognizing the molecular structure of antigens to produce antigen-specific antibodies, and plays the most important role in the humoral immune system.

As used herein, the term "epitope" refers to a localized region of an antigen to which an antibody or a fragment thereof may specifically bind. Epitopes usually consist of surface groups of molecules, such as amino acids or sugar side chains, and usually have specific three-dimensional structural characteristics, as well as specific charge characteristics. Conformational and non-conformational epitopes are distinguished in that the binding to conformational epitopes but not non-conformational epitope is lost in the presence of denaturing solvents. The epitopes may include amino acid residues directly involved in the binding (also called an immunodominant component of an epitope) and other amino acid residues not directly involved in the binding, for example, amino acid residues effectively blocked by the specific antigen binding peptide (that is, the amino acid residue is present within the footprint of the specific antigen binding peptide).

Hereinafter, the present invention will be described in detail with reference to examples. However, the following examples are illustrative only and do not limit the scope of the present invention.

Example 1

Preparation of Deimmunized Flagellin

For the development of deimmunized flagellin, flagellin B (FlaB), a flagellin protein of *Vibrio vulnificus*, was deimmunized.

The bacterial strains, plasmids, and influenza virus used in the present invention are shown in Table 1.

TABLE 1

| | | Characteristics | Source |
|---|---|---|---|
| Bacteria | *Escherichia coli* DH5α | F⁻ recA1 restriction negative | Laboratory collection |
| | *E. coli* ER2566 | F⁻ λ⁻ fhuA2 [lon] ompT lacZ::T7 gene1 gal sulA1ᐃ (mcrC-mrr)114::IS10 R(mcr-73::miniTn10-TetS)2R(zgb-210::Tn10)(TetS) endA1 [dcm] | New England Biolabs, Inc. |
| | *E. coli* BL21 (DE3) | hsdS gal (λclts857 ind1 Sam7 nin5 lacUV5-T7 gene1) | Laboratory collection |
| Plasmid | pCR2.1TOPO | Cloning vector; Apʳ; Kmʳ | Invitrogen |
| | pTYB12 | N-terminal fusion expression vector in which the N terminus of a target protein is a fused Intein-tag; Apʳ | New England Biolabs, Inc. |
| | pET30a+ | N-terminal fusion expression vector in which the N terminus of a target protein is a fused His-tag; Kmʳ | EMD Bioscience |

TABLE 1-continued

| | | Characteristics | Source |
|---|---|---|---|
| | pCMM250 | 1.5-kb EcoRI-Pstl fragment containing ORF of flaB cloned into pTYB12 | This study |
| | pET-30a(+)::dFlaB | pET-30a(+) plasmid containing a DNA-fragment of FlaB with deletion of spanned 175-193 amino acid at Ndel-Xhol | This study |
| | pET-30a(+)::FlaB$^{\Delta D2D3}$ | pET-30a(+) plasmid containing a DNA-fragment of FlaB with deletion of D2D3 region at Ndel-Xhol | This study |
| Influenza virus | H1N1 | A/Brisbane/59/2007 | Centers for Disease Control and Prevention |

1-1. Discrimination of B3-Cell Epitope for Deimmunization

Figure 1:
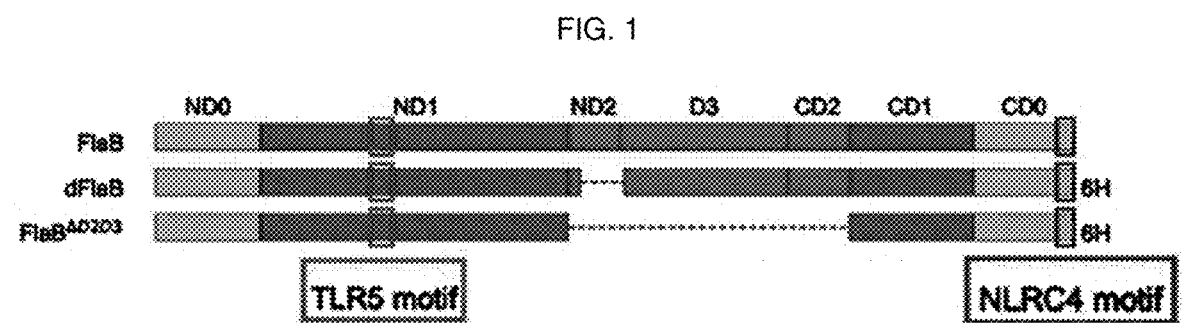
Figure 2:
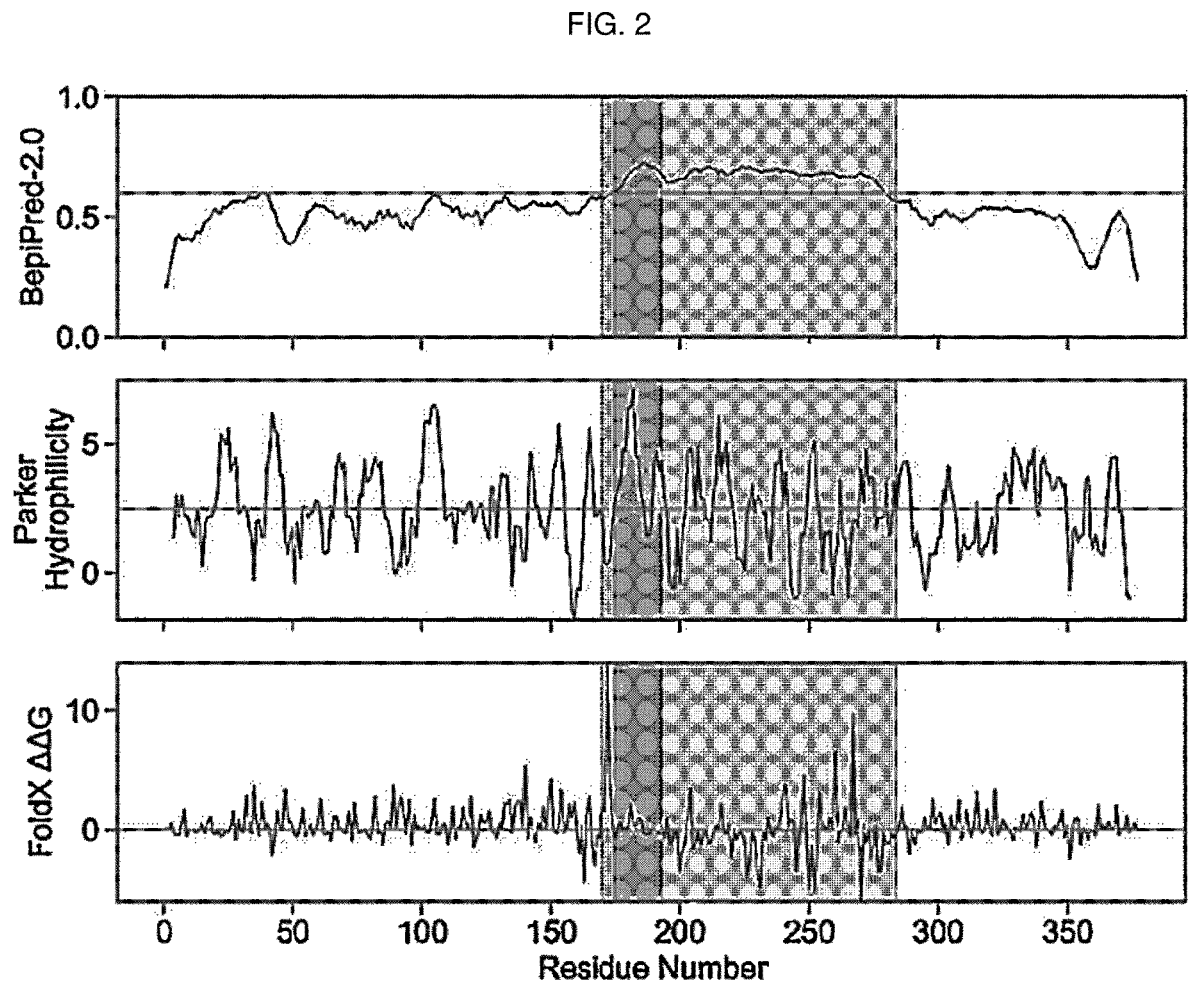

As shown in FIGS. 1 and 2, potential B-cell epitope of FlaB was identified using BepiPred 2.0, Parker hydrophilicity and alanine scanning. As a result, the ND2 to CD2 domain (ND2-D3-CD2) was predicted to contain predominant B cell epitopes. Among these, a specific region was identified and a 19 amino acid region (175 SYQAEEGKDKNWNVAAGDN 193, SEQ ID NO: 1) and is shown in Table 2.

TABLE 2

| SEQ ID NO | Amino acid sequence |
|---|---|
| SEQ ID NO: 1 | SYQAEEGKDKNWNVAAGDN |

As shown in FIG. 1, the deimmunized flagellins, FlaB$^{\Delta D2D3}$ in which the ND2 to CD2 domains (ND2-D3-CD2) were deleted and dFlaB in which the amino acid sequence of SEQ ID NO: 1 was deleted, were prepared.

1-2. Plasmid Construction and Recombinant Protein Production

Plasmids were maintained in *Escherichia coli* grown on Luria Bertani (LB) agar plates with ampicillin (100 μg/ml) and kanamycin (100 μg/ml). To construct expression vectors for FlaB$^{\Delta D2D3}$ and dFlaB, two sets of primers were designed to amplify the upstream or downstream region of the flaB gene. The primers were synthesized with overhangs recognized by specific restriction enzymes (REs). The upstream and downstream amplicons of flaB fragments were linked by cross-over PCR to generate nucleotide sequences corresponding to FlaB$^{\Delta D2D3}$ and dFlaB proteins. The purified PCR products were cloned into the pCR2.1 TOPO vectors (Invitrogen, Inc., Carlsbad, CA), and the fusion fragments were digested with an appropriate restriction enzyme (REs) and subcloned into the pET30a+ plasmids. The DNA sequences of the generated expression vectors were identified by dideoxy-chain termination sequencing using the Macrogen Online Sequencing Order System (http://dna.macrogen.com/kor/). The generated expression plasmids were transformed into competent *E. coli* BL21. Protein expression was performed by culturing cells with 0.1 mM isopropyl-β-D-thiogalactoside (IPTG) at 20° C. for 18 hours, and the cells were pelletized by centrifugation and stored at −80° C. before use. The bacterial pellets were lysed by 50 mL of a lysis buffer (pH 8, 50 mM NaH$_2$PO$_4$, 300 mM NaCl and 10 mM imidazole, 0.1% TritonX-100, 0.1% Tween, and 20 μM phenylmethylsulfonyl fluoride). After centrifugation at 18,000 rpm for 30 minutes, cell-free supernatants were loaded onto a column containing Ni-NTA agarose beads (Qiagen, Hilden, Germany) according to the manufacturer's instructions. The purity of the recombinant proteins was identified using sodium dodecyl sulfate-polyacrylamide gel electrophoresis (SDS-PAGE) and native-gel electrophoresis (native-PAGE), and subsequent Western blotting using anti-FlaB antibody produced in mice using complete Freund's adjuvant (Sigma-Aldrich, St. Louis, MO). The column-purified protein buffer was exchanged with phosphate-buffered saline (PBS) by a centrifugal filter tube (Amicon® Ultra-15 Centrifugal Filter, 10 k). Lipopolysaccharide (LPS) contamination was removed by treatment with Triton X-114 (Sigma-Aldrich, St. Louis, MO), and the traces of Triton X-114 were removed by culturing 1 mL of the protein with 0.3 g of Bio-Beads™-2 (Bio-Rad Laboratories, Inc., Hercules, CA) and treatment with Bio-Beads™ SM-2 according to the manufacturer's instructions. The residual LPS content was determined using a gel-coagulated Endosafe LAL kit (Charles River, Charleston, SC). The LPS levels in protein preparations were maintained below FDA guidelines (0.15 EU/30 g per mouse).

Example 2

Characterization of Deimmunized Flagellins

To characterize the deimmunized flagellins dFlaB and FlaB$^{\Delta D2D3}$ prepared in Example 1, SDS-PAGE, native-PAGE, and Western blotting were performed as follows.

The bacterial pellets prepared in Example 1 were lyzed by 50 mL of a lysis buffer (pH 8, 50 mM NaH$_2$PO$_4$, 300 mM NaCl and 10 mM imidazole, 0.1% TritonX-100, 0.1% Tween, and 20 μM phenylmethylsulfonyl fluoride). After centrifugation at 18,000 rpm for 30 minutes, cell-free supernatants were loaded onto a column containing Ni-NTA agarose beads (Qiagen, Hilden, Germany) according to the manufacturer's instructions. Sodium dodecyl sulfate-polyacrylamide gel electrophoresis (SDS-PAGE) and native-gel electrophoresis (native-PAGE), and subsequent Western blotting using anti-FlaB antibody produced in mice using complete Freund's adjuvant (Sigma-Aldrich, St. Louis, MO) were performed, and the results are shown in FIG. 3.

As shown in FIG. 3, the results of SDS-PAGE of wild-type flagellin (FlaB), dFlaB, and FlaB$^{\Delta D2D3}$, dFlaB of the present invention had an estimated molecular weight of 40.7 kDa, which was smaller than a molecular weight of FlaB of 41.47 kDa, but showed slower mobility on SDS-PAGE. However, as a result of native-PAGE, FlaB showed a large multimer whereas dFlaB and FlaB$^{\Delta D2D3}$ of the present invention were present as smaller multimers. In addition, as a result of Western blotting following SDS-PAGE and native-PAGE, dFlaB showed fainter bands than Flab, and FlaB$^{\Delta D2D3}$ showed even fainter bands.

It was therefore identified that: dFlaB and FlaB$^{\Delta D2D3}$ of the present invention showed the inhibition of polymerization of flagellin; considering the results of FlaB$^{\Delta D2D3}$, D2 and D3 domains of FlaB were more antigenic; and considering the results of dFlaB, the amino acid sequence of SEQ ID NO: 1 played a dominant role in inducing the FlaB-specific antibody response.

Example 3

Identification of TLR5 Stimulatory Activity of Deimmunized Flagellins

To identify the Toll-like receptor 5 (TLR5) stimulatory activity of the de-immune flagellins dFlaB and FlaB$^{\Delta D2D3}$ prepared in Example 1, the activity level of NF-ζB, a key factor involved in TLR5-mediated signaling, was measured as follows.

After 293T cells were dispensed at $2 \times 10^5$/well in a 24-well plate and cultured for 24 hours, the cells were transfected with p3×Flag-hTLR5 (100 ng/well), pNFζB-luc (100 ng/well), and 50 ng/well pCMV-β-Gal by using Effectene (Qiagen, Hilden Germany) at 5 μl/well. 24 Hours after transfection, the culture media were removed and replaced with serum-free Gibco® DMEM (Thermo Fischer Scientific Inc. Waltham, MA). The cells were treated with FlaB, dFlaB, and FlaB$^{\Delta D2D3}$ and cultured for 24 hours, and PBS-treated cells were used as a control group. The media were removed, and then the cells were treated with 100 μl/well 1×lysis buffer (Promega, Madison, WI) and maintained at room temperature for 1 hour. To determine NF-ζB activation, 30 μL of the cell lysate was transferred to a 96-well opaque plate for the measurement of luciferase activity, and another 30 μL of the cell lysate was transferred to a 96-well cell culture plate for β-Gal measurement. The luciferase activity was normalized to LacZ expression using the control group expressing plasmid pCMV-β-Gal (Clontech, Takara Bio, Kyoto, Japan). The luciferase activity was measured by a luminometer (MicroLumatPlus LB 96V; Berthold, Wilbad, Germany), and β-Gal was read at 420 nm by a microplate reader (Molecular Devices Corp., Menlo Park, CA). The experimental results are shown FIG. 4.

Figure 4:
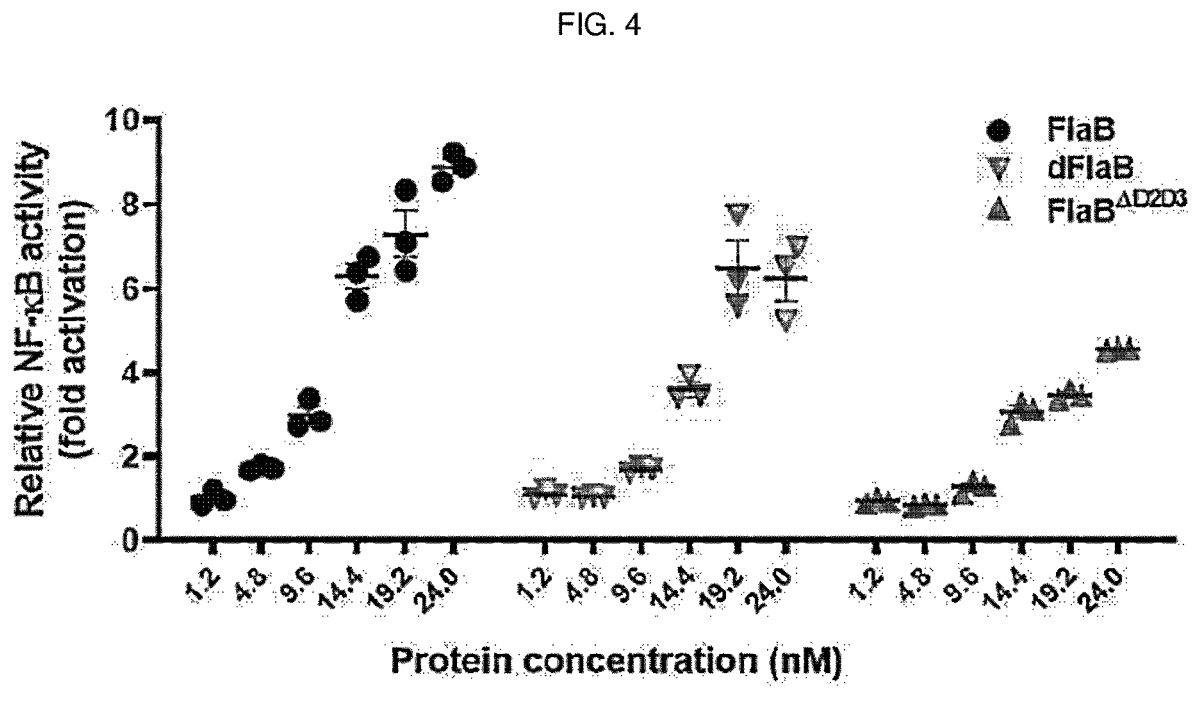

As shown in FIG. 4, as a result of measuring the NF-ζB activity levels by FlaB, dFlaB, and FlaB$^{\Delta D2D3}$, it was identified that dFlaB and FlaB$^{\Delta D2D3}$ induced NF-ζB activity in a dose-dependent manner, indicating that TLR5-stimulatory activity was maintained.

Ultimately, dFlaB and FlaB$^{\Delta D2D3}$ exhibited similar biological activity to FlaB by maintaining TLR5-stimulatory activity.

Example 4

Identification of Induction of FlaB-Specific Immune Response In Vivo by Deimmunized Flagellins In order to identify whether the deimmunized flagellins dFlaB and FlaB$^{\Delta D2D3}$ prepared in Example 1 induced a FlaB-specific immune response in vivo, 7-week-old female Balb/c mice (OrientBio, Seongnam, Korea) were intranasally immunized with 4 μg of the flagellin proteins seven times at two-week intervals, and ELISPOT analysis, Western blotting, and ELISA were performed as follows.

4-1. ELISPOT Analysis

After the Balb/c mouse groups were immunized three times at two-week intervals as described above, IgG- or IgA-secreting bone marrow plasma cells and spleen memory B cells were measured. To determine FlaB-specific antibody-secreting cells (ASCs), a multi-screen 96-well plate (BD Biosciences) was coated with FlaB, dFlaB, or FlaB$^{\Delta D2D3}$ (1 μg/well) at 4° C. overnight. The plate was blocked with RPMI1640 (Thermo Fischer Scientific Inc. Waltham, MA) supplemented with 10% fetal bovine serum (Thermo Fischer Scientific Inc. Waltham, MA), and then $10^6$ spleen cells or $10^6$ bone marrow cells were added to the FlaB-coated plate and then cultured for 24 hours for bone marrow cells or 5 days for spleen cells. Thereafter, the plate was incubated with HRP-conjugated anti-mouse IgG or IgA according to the manufacturer's protocol, and spots were visualized by AEC substrate (BD Biosciences, BD, Franklin Lakes, NJ) and counted by a CTL-Immunospot Analyzer (Cellular Technology, Shaker Heights, OH). The experimental results are shown in Tables 3 and 4 and FIG. 5.

TABLE 3

| | FlaB-specific IgG-secreting plasma cells (spots/$10^6$ cells) | FlaB-specific IgG-secreting memory B cells (spots/$10^6$ cells) |
|---|---|---|
| FlaB | 16.50 ± 1.19 | 14.75 ± 1.80 |
| FlaB$^{\Delta D2D3}$ | 2.50 ± 0.87 | 0.50 ± 0.29 |
| dFlaB | 0.75 ± 0.25 | 0.25 ± 0.25 |

TABLE 4

| | FlaB-specific IgA-secreting plasma cells (spots/$10^6$ cells) | FlaB-specific IgA-secreting memory B cells (spots/$10^6$ cells) |
|---|---|---|
| FlaB | 17.75 ± 3.63 | 36.25 ± 9.25 |
| FlaB$^{\Delta D2D3}$ | 1.41 ± 0.82 | 2.00 ± 1.25 |
| dFlaB | 0.50 ± 0.29 | 0.25 ± 0.29 |

Figure 5:
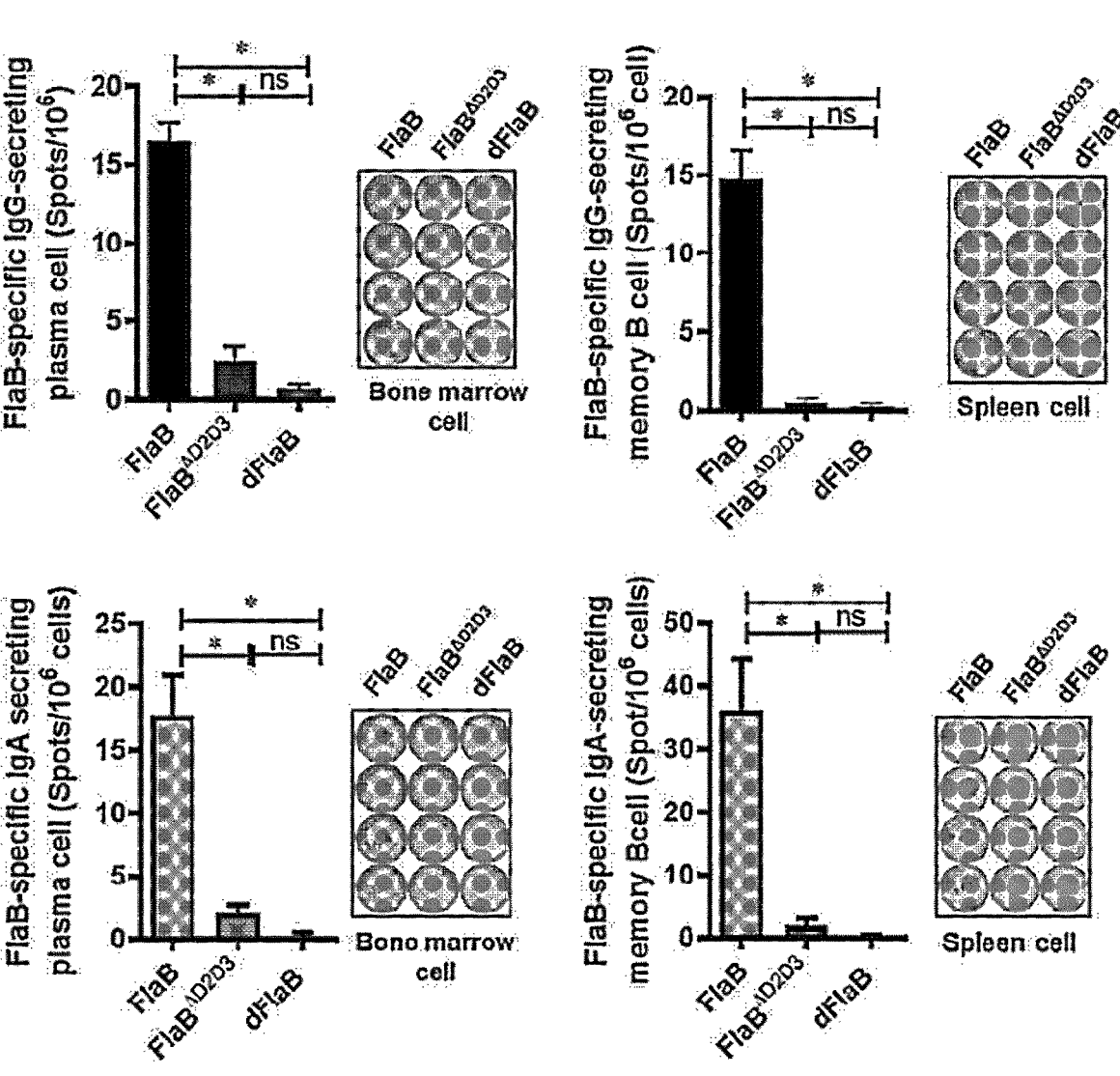
FIGS. 5, 6 and 7 show ELISPOT, Western blotting, and ELISA results of analyzing FlaB-specific immune responses of FlaB, dFlaB, and FlaBΔD2D3.

As shown in Tables 3 and 4 and FIG. 5, as a result of measuring FlaB-specific IgG- or IgA-secreting cells by FlaB, dFlaB, and FlaB$^{\Delta D2D3}$, it was observed that the number of FlaB-specific IgG- or IgA-secreting cells was significantly reduced for dFlaB and FlaB$^{\Delta D2D3}$ compared with FlaB, and especially, the number was smallest for dFlaB. Therefore, dFlaB and FlaB$^{\Delta D2D3}$ of the present invention hardly induced the FlaB-specific immune response in vivo.

4-2. Western Blotting

To identify whether FlaB-specific antibodies were not continuously induced through the multiple immunization, mice were immunized with FlaB, dFlaB, or FlaB$^{\Delta D2D3}$ six times at two-week intervals and then Western blotting was performed using anti-sera from the immunized mice. The experimental results are shown FIG. 6.

Figure 6:
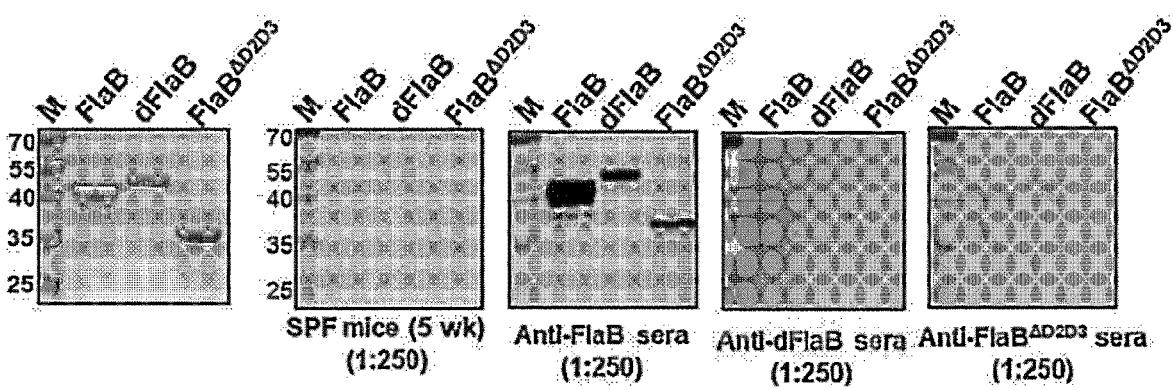

As shown in FIG. 6, anti-FlaB sera recognized corresponding FlaB, dFlaB, and FlaB$^{\Delta D2D3}$ proteins, wherein FlaB showed a strong-intensity band but dFlaB and FlaB$^{\Delta D2D3}$ showed weaker-intensity bands. It can be therefore seen that D2 and D3 domains of FlaB play a dominant role in inducing the FlaB-specific antibody response.

It was also identified that anti-dFlaB sera and anti-FlaB$^{\Delta D2D3}$ sera hardly detected FlaB, dFlaB, or FlaB$^{\Delta D2D3}$ protein, indicating similar patterns to those recognized in normal naive sera.

4-3. ELISA

Mice were immunized with FlaB, dFlaB, or FlaB$^{\Delta D2D3}$ seven times at two-week intervals and then ELISA was performed using anti-sera from the immunized mice. The FlaB-, dFlaB-, or FlaB$^{\Delta D2D3}$-specific serum IgG titer was measured in anti-FlaB, anti-dFlaB, and anti-FlaB$^{\Delta D2D3}$ sera, and the results are shown in Table 5 and FIG. 7.

TABLE 5

| | FlaB-specific IgG (reciprocal log2titer) | dFlaB-specific IgG (reciprocal log2 titer) | FlaB$^{\Delta D2D3}$-specific IgG (reciprocal log2 titer) |
|---|---|---|---|
| FlaB | 12.00 ± 0.89 | 10.4 ± 0.93 | 10.8 ± 0.80 |
| dFlaB | 6.0 ± 0.0 | 5.4 ± 0.24 | 6.0 ± 0.32 |
| FlaB$^{\Delta D2D3}$ | 5.8 ± 0.20 | 5.2 ± 0.20 | 5.8 ± 0.32 |

Figure 7:
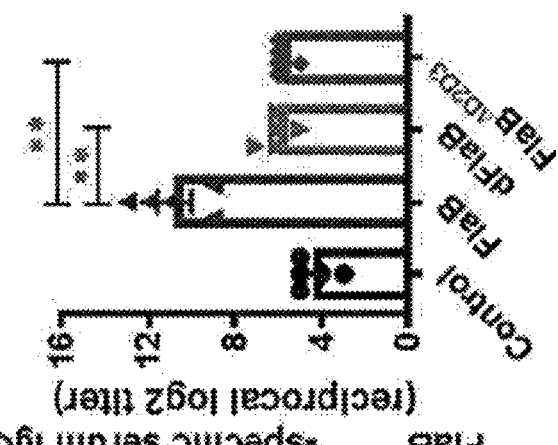
Figure 7:
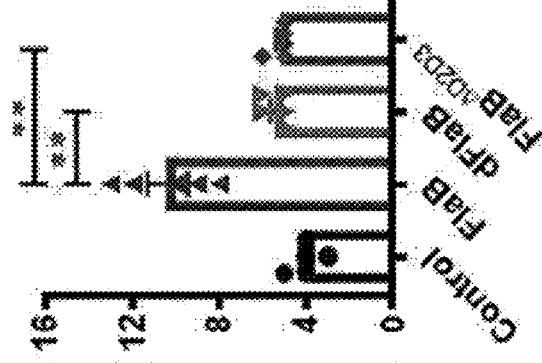
Figure 7:
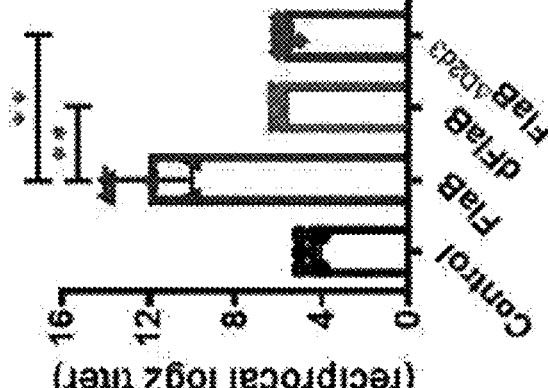

As shown in Table 5 and FIG. 7, FlaB-specific serum IgG levels in dFlaB and FlaB$^{\Delta D2D3}$ were significantly reduced compared with that in FlaB. It was therefore identified that dFlaB and FlaB$^{\Delta D2D3}$ were significantly weakened in inducing FlaB-specific serum IgG even after seven repeated intranasal immunizations.

The experimental results identified that dFlaB and FlaB$^{\Delta D2D3}$ of the present invention did not induce the FlaB-specific immune response in vivo, and particularly, did not induce an immune response even upon repeated immunization. It can be also seen that the amino acid sequence of SEQ ID NO: 1 or D2 and D3 domains including the same are an essential B-cell epitope and play a role in binding to anti-FlaB antibodies, and particularly, the production of FlaB-specific antibodies can be inhibited simply by a deletion of the amino acid of SEQ ID NO: 1.

Example 5

Identification of Mucosal Vaccine Adjuvant Activity of Deimmunized Flagellin

In order to identify the activity, as a mucosal vaccine adjuvant, of the deimmunized flagellin dFlaB prepared in Example 1, 7-week-old female Balb/c mice (OrientBio, Seongnam, Korea) were intranasally immunized with PBS, 4 µg of dFlaB, 4 µg of FlaB, and 1.5 µg of sH3N2 (H3N2 A/Switzerland/9715293/2013 NIB-88 split vaccine; IL-YANG PHARM. Yongin, Korea), 1.5 µg of sH3N2+4 µg of dFlaB, and 1.5 µg of sH3N2+4 µg of FlaB three times at two-week intervals, and then the sH3N2- or FlaB-specific antibody response in sera and bronchoalveolar lavage fluid (BALF) of each group was analyzed by ELISA and Western blotting as follows. The experimental results are shown in FIGS. 8 and 9.

Figure 8:
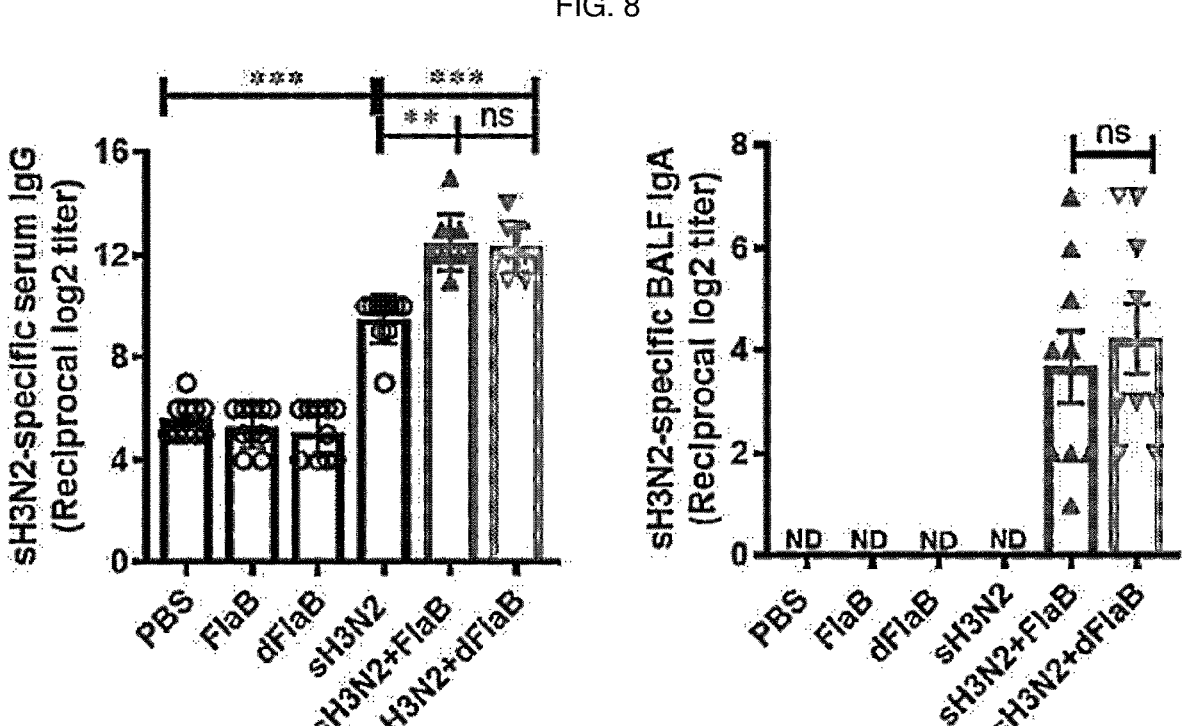
FIGS. 8 and 9 show ELISA and Western blotting results of analyzing sH3N2-specific antigen or FlaB-specific antibody responses when FlaB and dFlaB were used as mucosal vaccine adjuvants.

As shown in FIG. 8, as a result of ELISA, sH3N2-specific serum IgG was induced at a significantly high level for the combined administration of sH3N2 and FlaB or dFaB. In addition, the sH3N2-specific BALF IgA was induced for only the combined administration of sH3N2 and FlaB or dFaB, indicating that mucosal vaccine immune boosters affected the production of secretory IgA.

Figure 9:
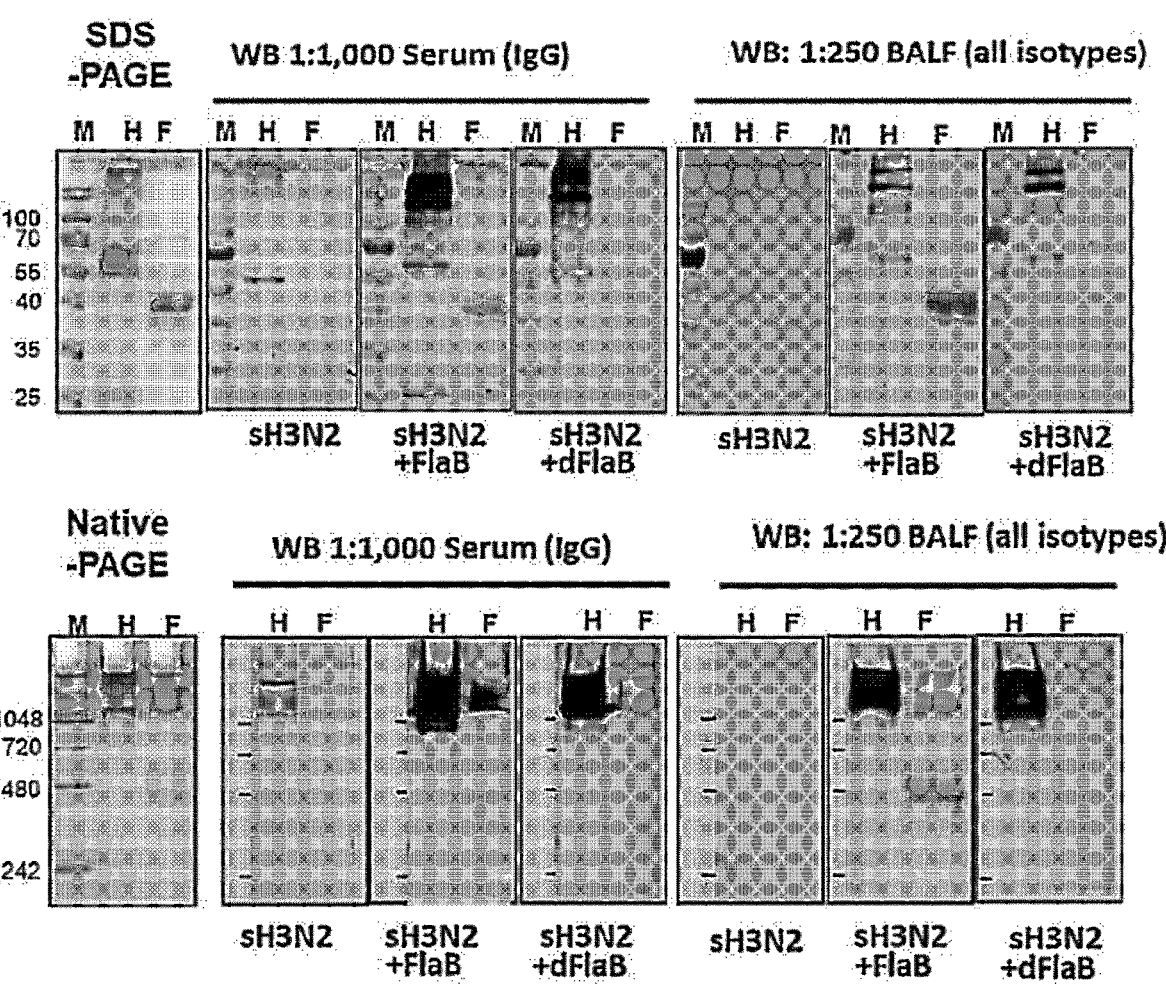

As shown in FIG. 9, as a result of anti-serum Western blotting following SDS-PAGE and native-PAGE, anti-sH3N2 sera detected sH3N2 antigen at weak binding strength, whereas anti-dFaB+sH3N2 or anti-FlaB+sH3N2 sera detected sH3N2 antigen at stronger binding strength. Unlike the anti-FlaB+sH3N2 sera detecting FlaB in both the anti-serum Western blotting following SDS-PAGE and native-PAGE, the anti-dFlaB+sH3N2 sera did not detect FlaB in the anti-serum Western blotting following SDS-PAGE and detected the minimum of FlaB in only the anti-serum Western blotting following native-PAGE.

As a result of anti-BALF Western blotting following SDS-PAGE and native-PAGE, anti-sH3N2 BALF hardly detected sH3N2 antigen, whereas anti-dFlaB+sH3N2 or anti-FlaB+sH3N2 BALF detected sH3N2 antigen at stronger binding strength. Unlike the anti-Flab+sH3N2 BALF detecting FlaB in both the anti-BALF Western blotting following SDS-PAGE and native-PAGE, the anti-dFlaB+sH3N2 BALF did not detect FlaB.

It can be therefore seen that dFlaB of the present invention can play an effective role as a mucosal vaccine adjuvant by exhibiting an effect as a vaccine immune booster at a similar level to FlaB and not inducing the FlaB-specific antibody response.

Example 6

Identification of Flu Vaccine Adjuvant Activity of Deimmunized Flagellin

To identify the activity, as a flu vaccine adjuvant, of the deimmunized flagellin prepared in Example 1, Balb/c mice were vaccinated with 4 µg of dFlaB+0.2 or 0.08 µg of H1N1A/Brisbane/59/07 split vaccine (Green Cross, Hwasun, Korea) (sH1N1+dFlaB), and 4 µg of FlaB+0.2 or 0.08 µg of sH1N1 (sH1N1+FlaB). After the mice were immunized three times at two-week intervals, serum samples were collected, and vaccinated mice were infected with live A/Brisbane/59/07 homologous influenza virus strain 2.4× LD$_{50}$. The mice were monitored for survival rates and body weight changes for 14 days after the influenza virus infection, and the results are shown in FIGS. 10 and 11.

Figure 10:
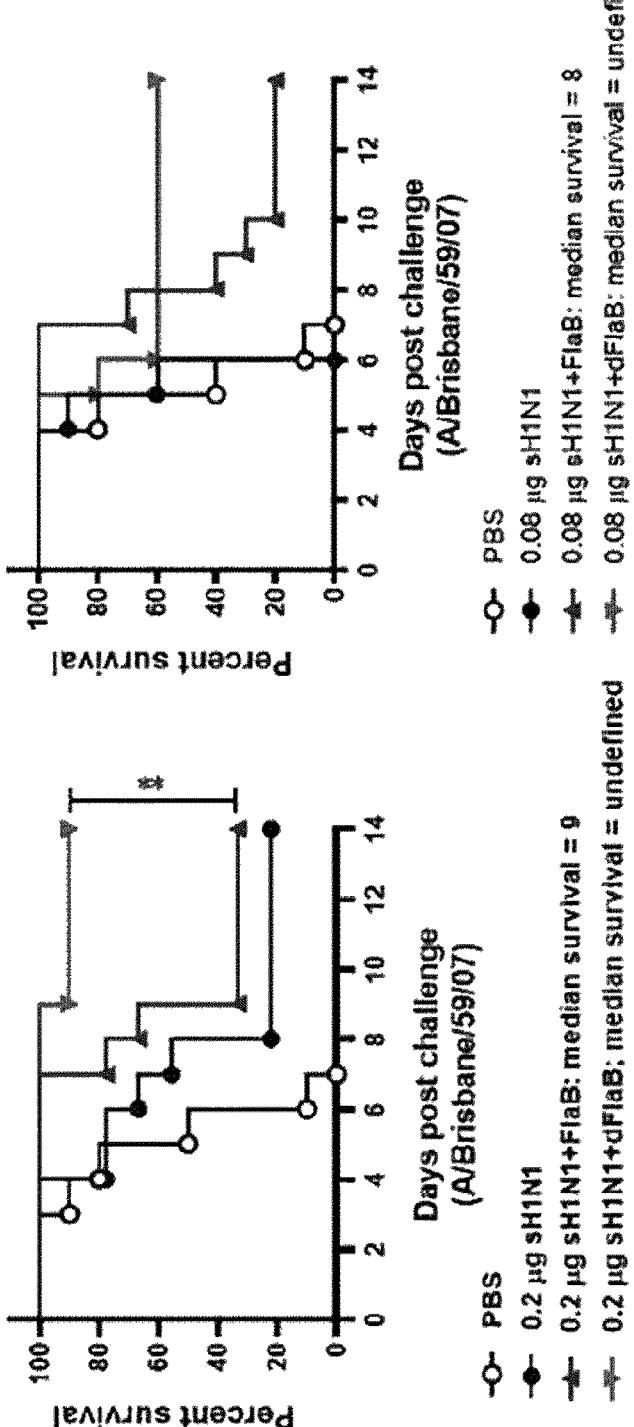
FIGS. 10 and 11 show survival rates and body weight changes of mice when FlaB and dFlaB were used as flu vaccine adjuvants, in a live virus challenge experiment.

As shown in FIG. 10, as a result of measuring survival rates, the final survival rates for 0.2 µg of sH1N1+dFlaB- or 0.2 µg of sH1N1+FlaB-vaccinated mice were 90% and 33.3%, respectively, whereas the final survival rates for 0.08 µg of sH1N1+dFlaB- or 0.08 µg of sH1N1+FlaB-vaccinated mice were 60% and 20%, respectively. Therefore, the sH1N1+dFlaB-immunized mice showed superior survival rates compared with the sH1N1+FlaB-immunized mice.

Figure 11:
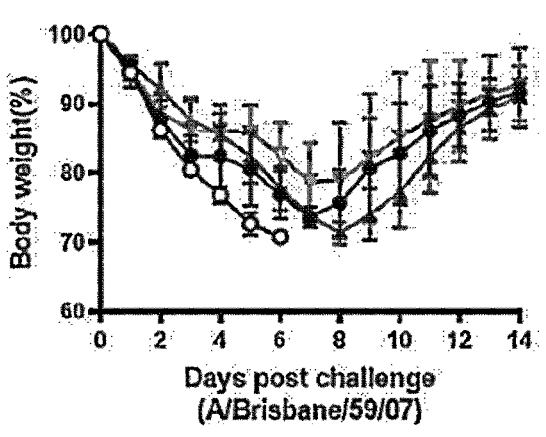
Figure 11:
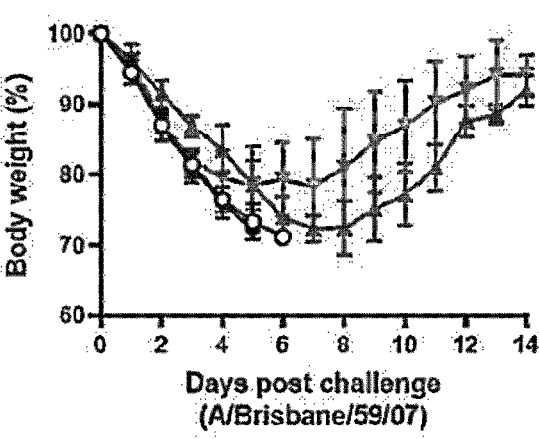

As shown in FIG. 11, as a result of measuring body weight changes, the sH1N1+dFlaB-immunized groups showed rapid body weight reductions at the early stage, but quickly regained body weights after 3 or 5 days.

It can be therefore seen that dFlaB of the present invention, when used together with a flu vaccine, can induce a protective immune function at a higher level than FlaB to thereby play an effective role as a flu vaccine adjuvant.

What is claimed is:

1. A flagellin variant derived from *Vibrio vulnificus* comprising: N-terminal domain 2, N-terminal domain 3, and C-terminal domain 2, wherein the amino acid sequence of SEQ ID NO: 1 is deleted from the flagellin variant.

2. The flagellin variant of claim 1, wherein the flagellin is flagellin B (FlaB).

3. The flagellin variant of claim 1, wherein the flagellin variant retains toll-like receptor 5 (TLR5) stimulatory activity.

4. The flagellin variant of claim 1, wherein the flagellin variant induces no flagellin-specific immune response.

5. The flagellin variant of claim 1, wherein the flagellin variant has an immune boosting effect.

6. A vaccine composition comprising the flagellin variant of claim 1 and at least one antigen.

7. A flu vaccine composition comprising the flagellin variant of claim 1 as an adjuvant.

\* \* \* \* \*

SEQUENCE LISTING

<160> NUMBER OF SEQ ID NOS: 1

<210> SEQ ID NO 1
<211> LENGTH: 19
<212> TYPE: PRT
<213> ORGANISM: Artificial Sequence
<220> FEATURE:
<223> OTHER INFORMATION: dFlaB

<400> SEQUENCE: 1

-continued

```
Ser Tyr Gln Ala Glu Glu Gly Lys Asp Lys Asn Trp Asn Val Ala Ala
1               5                   10                  15

Gly Asp Asn
```